(12) United States Patent
Lee

(10) Patent No.: US 11,932,686 B2
(45) Date of Patent: *Mar. 19, 2024

(54) USE OF REGULATORY T CELL-SPECIFIC SURFACE PROTEIN LRIG-1

(71) Applicant: GOOD T CELLS, INC., Seoul (KR)

(72) Inventor: Sang-kyou Lee, Seoul (KR)

(73) Assignee: Good T Cells, Inc., Seoul (KR)

( * ) Notice: Subject to any disclaimer, the term of this patent is extended or adjusted under 35 U.S.C. 154(b) by 210 days.

This patent is subject to a terminal disclaimer.

(21) Appl. No.: 17/374,224

(22) Filed: Jul. 13, 2021

(65) Prior Publication Data

US 2021/0340235 A1 Nov. 4, 2021

Related U.S. Application Data

(63) Continuation of application No. 16/233,738, filed on Dec. 27, 2018, now Pat. No. 11,091,538, which is a continuation of application No. 14/427,421, filed as application No. PCT/KR2012/000532 on Jan. 20, 2012.

(30) Foreign Application Priority Data

Jan. 24, 2011 (KR) .................. 10-2011-0007022

(51) Int. Cl.
| | |
|---|---|
| C07K 16/18 | (2006.01) |
| A61K 35/17 | (2015.01) |
| A61K 38/00 | (2006.01) |
| C07K 14/47 | (2006.01) |
| C12N 15/113 | (2010.01) |
| C12Q 1/6876 | (2018.01) |
| G01N 33/50 | (2006.01) |
| G01N 33/68 | (2006.01) |
| G01N 33/94 | (2006.01) |

(52) U.S. Cl.
CPC .............. *C07K 16/18* (2013.01); *A61K 35/17* (2013.01); *C07K 14/47* (2013.01); *C12N 15/113* (2013.01); *C12N 15/1138* (2013.01); *C12Q 1/6876* (2013.01); *G01N 33/5023* (2013.01); *G01N 33/505* (2013.01); *G01N 33/6854* (2013.01); *G01N 33/6872* (2013.01); *G01N 33/9493* (2013.01); *A61K 38/00* (2013.01); *C12N 2310/11* (2013.01); *C12N 2310/14* (2013.01); *C12N 2310/17* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 11,091,538 B2 * | 8/2021 | Lee | G01N 33/6854 |
| 2005/0048587 A1 * | 3/2005 | Rao | G01N 33/505 |
| | | | 435/7.21 |
| 2006/0083736 A1 | 4/2006 | Law et al. | |
| 2006/0204503 A1 | 9/2006 | Fitchett | |
| 2008/0113351 A1 | 5/2008 | Naito et al. | |
| 2014/0142160 A1 | 5/2014 | Lee et al. | |

FOREIGN PATENT DOCUMENTS

| | | |
|---|---|---|
| EP | 1930415 A1 | 11/2008 |
| WO | 2010022341 | 2/2010 |
| WO | 2010105298 A1 | 9/2010 |

OTHER PUBLICATIONS

Baan et al., "Differential Effect of Calaineurin Inhibitors, Anti-CD25 Antibodies and Rapamycin on the Induction of FOXP3 in Human T Cells", Transplantation, vol. 80, No. 1, pp. 110-117, Jul. 15, 2005*.
Cai et al., "Inhibition of LRIG3 gene expression via RNA interference modulates the proliferation, cell cycle, cell apoptosis, adhesion and invasion of glioblastoma cell (GL15)", Cancer Letters, vol. 278, pp. 104-112, (2009)*.
Guo et al., "Perinuclear leucine-rich repeats and immunoglobulin-like domain proteins [LRIG1-3] as prognostic indictors in astrocytic tumors", Acta Neuropathol., vol. 111, pp. 238-246, (2006)*.
Ledda et al, "Lrig1 is an Endogenous Inhibitor of Ret Receptor Tyrosine Kinase Activation, Downstream Signaling, and Biological Responses to GDNF", The Journal of Neuroscience, vol. 28, No. 1, pp. 39-49, Jan. 2, 2008*.
Nilsson et al, "Cloning, Characterization, and Expression of Human LIG1", Biochemical and Biophysical Research Communications, vol. 284, pp. 1155-1161, May 23, 2001*.
Sadlon et al., "Genome-Wide Identification of Human FOXP3 Target Cells in Natural Regulatory T Cells", The Journal of Immunology, vol. 185, pp. 1071-1081, Jun. 16, 2010*.
Valzasina et al., "Triggering of OX40 (CD134) on CD4+CD25+ T cells blocks their inhibitory activity: a novel regulatory role for OX40 and its comparison with GITR", Blood, vol. 105, No. 7, pp. 2845-2851, Apr. 1, 2005*.
Yang et al., "LRIG 1, a candidate tumour-suppesor gene in human bladder cancer cell line BIU87", Journal Compilation, pp. 898-902, (2006)*.
Focosi et al., "Immunosuppresive monoclonal antibodies: current and next generation", Clinical Microbiology and Infection, vol. 17, No. 12, pp. 1759-1768, Dec. 2011*.

(Continued)

*Primary Examiner* — Amy E Juedes
(74) *Attorney, Agent, or Firm* — Lathrop GPM LLP; Lisa Hillman

(57) ABSTRACT

The present invention relates to a novel use of regulatory T cell-specific surface protein Lrig-1, and more specifically to an immunosuppressive agent comprising siRNA which inhibits the expression of surface protein Lrig-1. In addition, the invention relates to a method for screening an immunosuppressive agent which inhibits proteins of Lrig-1 or genes encoding the proteins. As a result, an immunosuppressive agent with low side effects and high specificity can be developed.

5 Claims, 11 Drawing Sheets

Specification includes a Sequence Listing.

(56) References Cited

OTHER PUBLICATIONS

Scott et al, "Antibody Therapy of Cancer", Nature, vol. 12, pp. 278-287, Apr. 2012*.
Mor, 2005, Identification of aldolase as a target antigen in Alzheimer's disease J. Immunol. vol. 175: 3439-3445.
Chevalier, 2013, The split personality of regulatory T cells in HIV infection, Blood, vol. 121: 29-37.
U.S. Appl. No. 17/575,039, Non-Final Office Action dated May 16, 2023, 13 pages.

* cited by examiner

[Fig 1]
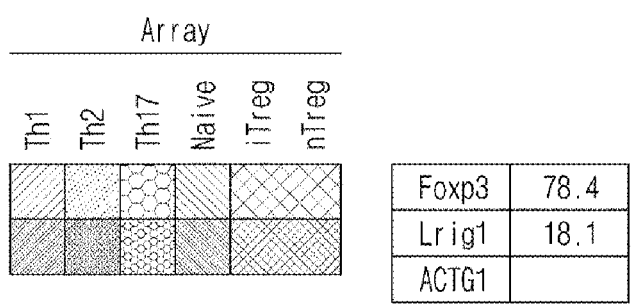

[Fig 2]
(a)
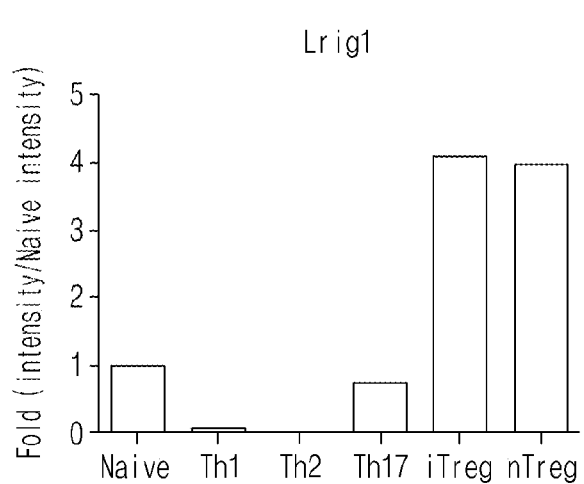
(b)
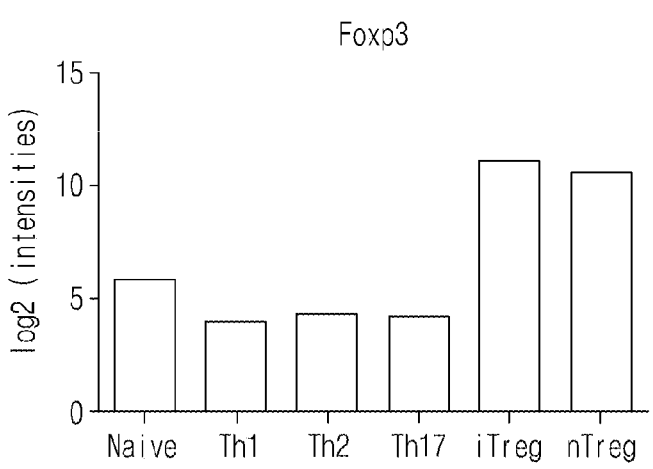

[Fig 3]
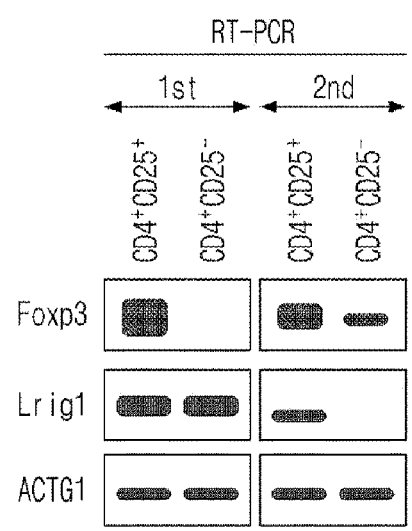

[Fig 4]
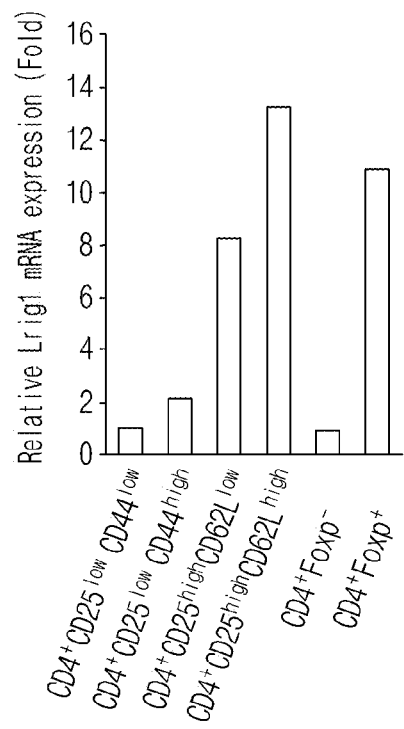

[Fig 5]
(a)
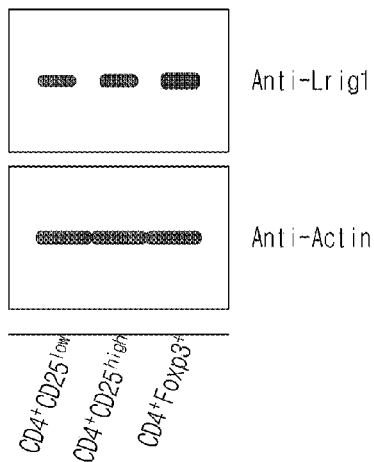
(b)
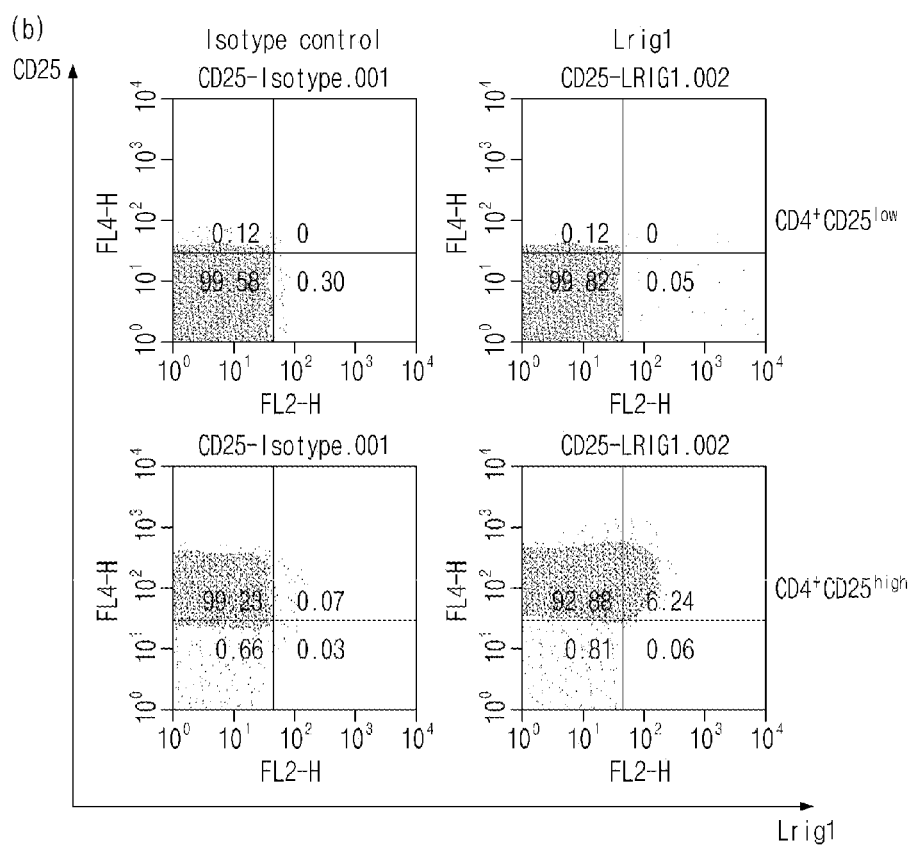

[Fig 6]
(a) Expanded Treg
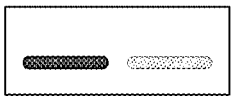 Lrig1
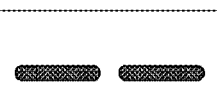 Foxp3
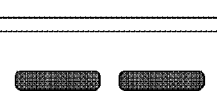 ACTG1
(b)
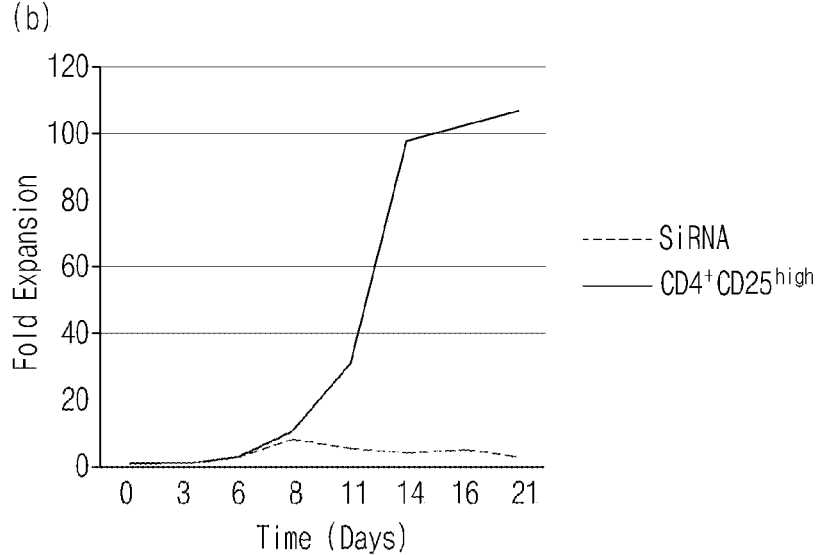

Fig. 7
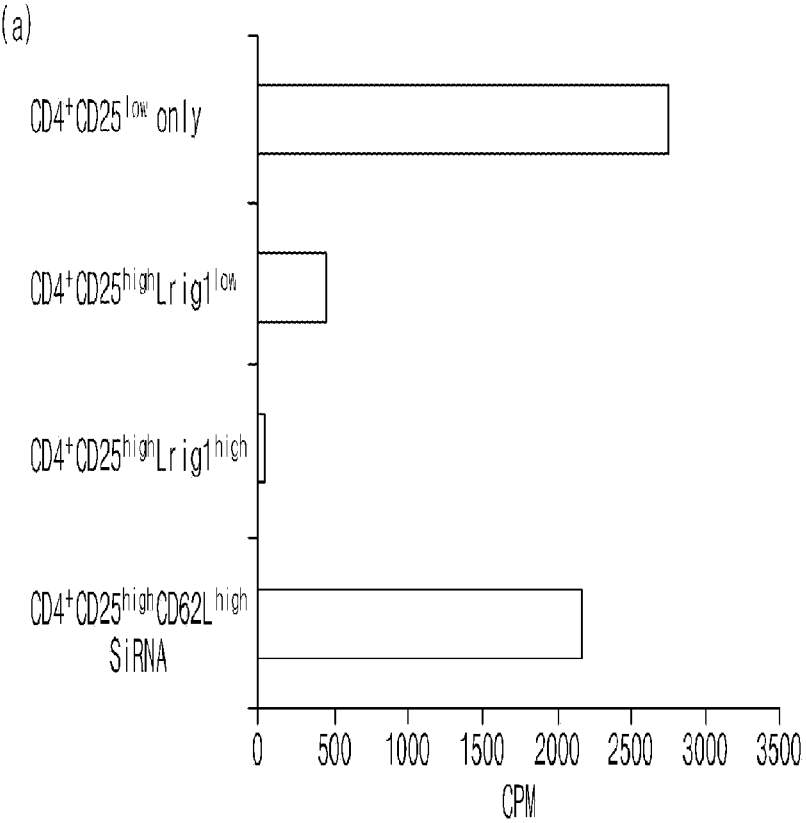
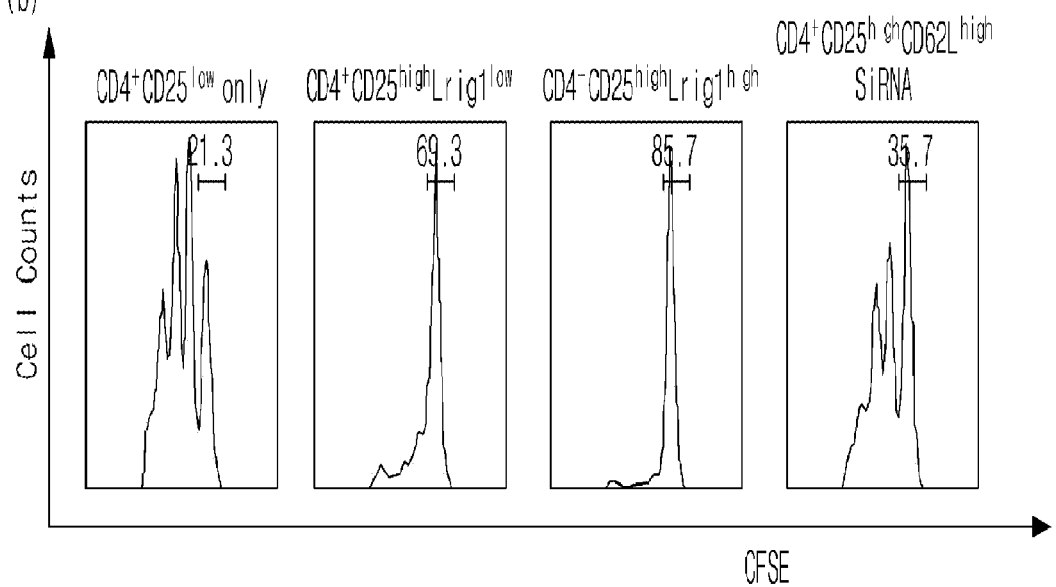

[Fig 8]
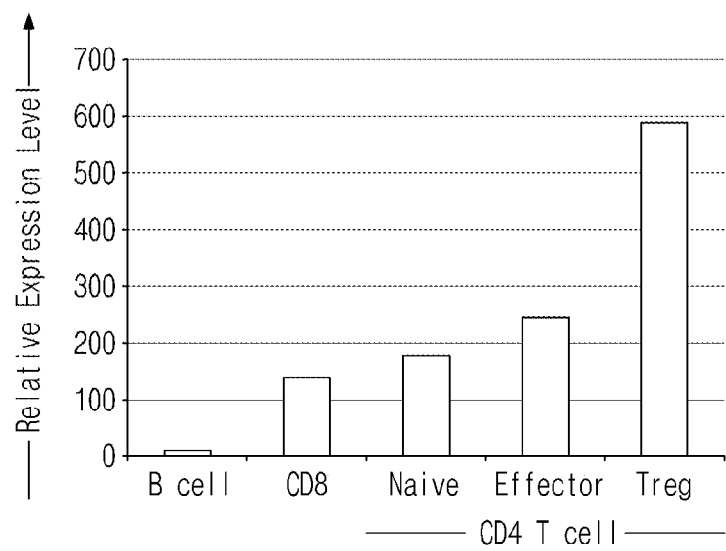

[Fig 9]
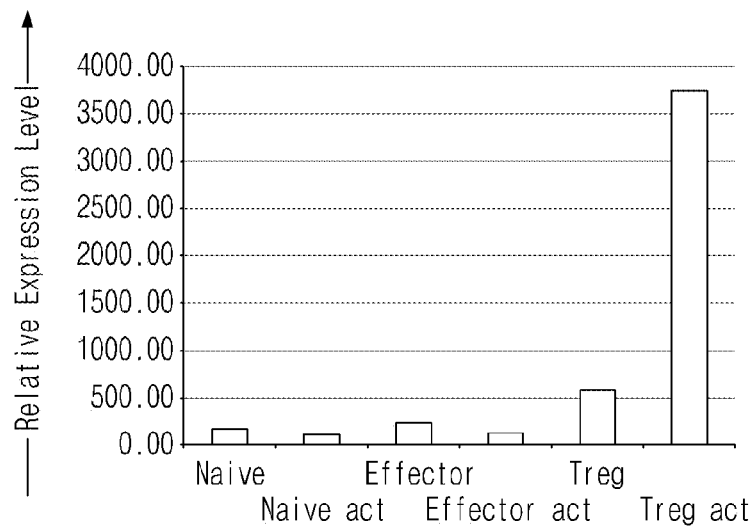

[Fig 10]
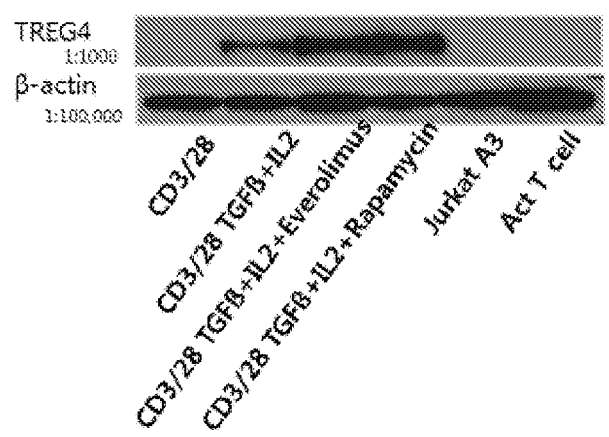

[Fig. 11]
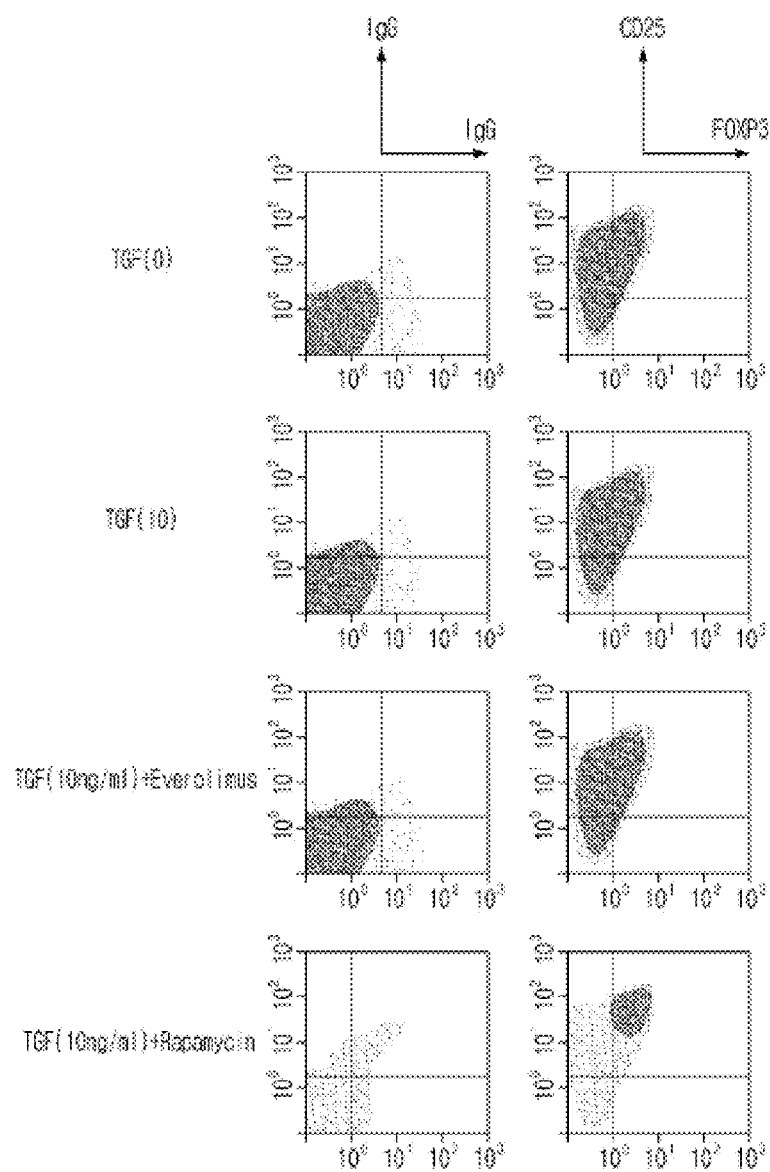

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
accaccgtag gcatcttcac                                                   20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gagccactgt gtgctgttgt                                                   20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cccttggccc atccccagga                                                   20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ccgagcgtgg gaaggtgcag                                                   20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ggcgtcatgg tgggcatggg                                                   20
```

```
<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
atggcgtggg gaagggcgta                                                  20

<210> SEQ ID NO 7
<211> LENGTH: 19
<212> TYPE: RNA
<213> ORGANISM: Artificial Sequence
<220> FEATURE:
<223> OTHER INFORMATION: siRNA J--046693-09

<400> SEQUENCE: 7
ccgaacggcc ugcguauaa                                                   19

<210> SEQ ID NO 8
<211> LENGTH: 19
<212> TYPE: RNA
<213> ORGANISM: Artificial Sequence
<220> FEATURE:
<223> OTHER INFORMATION: siRNA J-046693-10

<400> SEQUENCE: 8
ggagccagcu gaagucgua                                                   19

<210> SEQ ID NO 9
<211> LENGTH: 19
<212> TYPE: RNA
<213> ORGANISM: Artificial Sequence
<220> FEATURE:
<223> OTHER INFORMATION: siRNA J-046693-11

<400> SEQUENCE: 9
ggucuguagu ugaggacga                                                   19

<210> SEQ ID NO 10
<211> LENGTH: 19
<212> TYPE: RNA
<213> ORGANISM: Artificial Sequence
<220> FEATURE:
<223> OTHER INFORMATION: siRNA J-046693-12

<400> SEQUENCE: 10
ccuggaaggu gacggagaa                                                   19

<210> SEQ ID NO 11
<211> LENGTH: 1093
<212> TYPE: PRT
<213> ORGANISM: Homo sapiens

<400> SEQUENCE: 11

Met Ala Arg Pro Val Arg Gly Gly Leu Gly Ala Pro Arg Arg Ser Pro
1               5                   10                  15

Cys Leu Leu Leu Leu Trp Leu Leu Leu Leu Arg Leu Glu Pro Val Thr
            20                  25                  30

Ala Ala Ala Gly Pro Arg Ala Pro Cys Ala Ala Ala Cys Thr Cys Ala
        35                  40                  45

Gly Asp Ser Leu Asp Cys Gly Gly Arg Gly Leu Ala Ala Leu Pro Gly
```

```
            50                  55                  60
Asp Leu Pro Ser Trp Thr Arg Ser Leu Asn Leu Ser Tyr Asn Lys Leu
 65                  70                  75                  80

Ser Glu Ile Asp Pro Ala Gly Phe Glu Asp Leu Pro Asn Leu Gln Glu
                     85                  90                  95

Val Tyr Leu Asn Asn Asn Glu Leu Thr Ala Val Pro Ser Leu Gly Ala
                100                 105                 110

Ala Ser Ser His Val Val Ser Leu Phe Leu Gln His Asn Lys Ile Arg
                115                 120                 125

Ser Val Glu Gly Ser Gln Leu Lys Ala Tyr Leu Ser Leu Glu Val Leu
            130                 135                 140

Asp Leu Ser Leu Asn Asn Ile Thr Glu Val Arg Asn Thr Cys Phe Pro
145                 150                 155                 160

His Gly Pro Pro Ile Lys Glu Leu Asn Leu Ala Gly Asn Arg Ile Gly
                165                 170                 175

Thr Leu Glu Leu Gly Ala Phe Asp Gly Leu Ser Arg Ser Leu Leu Thr
                180                 185                 190

Leu Arg Leu Ser Lys Asn Arg Ile Thr Gln Leu Pro Val Arg Ala Phe
            195                 200                 205

Lys Leu Pro Arg Leu Thr Gln Leu Asp Leu Asn Arg Asn Arg Ile Arg
210                 215                 220

Leu Ile Glu Gly Leu Thr Phe Gln Gly Leu Asn Ser Leu Glu Val Leu
225                 230                 235                 240

Lys Leu Gln Arg Asn Asn Ile Ser Lys Leu Thr Asp Gly Ala Phe Trp
                245                 250                 255

Gly Leu Ser Lys Met His Val Leu His Leu Glu Tyr Asn Ser Leu Val
                260                 265                 270

Glu Val Asn Ser Gly Ser Leu Tyr Gly Leu Thr Ala Leu His Gln Leu
            275                 280                 285

His Leu Ser Asn Asn Ser Ile Ala Arg Ile His Arg Lys Gly Trp Ser
            290                 295                 300

Phe Cys Gln Lys Leu His Glu Leu Val Leu Ser Phe Asn Asn Leu Thr
305                 310                 315                 320

Arg Leu Asp Glu Glu Ser Leu Ala Glu Leu Ser Ser Leu Ser Val Leu
                325                 330                 335

Arg Leu Ser His Asn Ser Ile Ser His Ile Ala Glu Gly Ala Phe Lys
                340                 345                 350

Gly Leu Arg Ser Leu Arg Val Leu Asp Leu Asp His Asn Glu Ile Ser
            355                 360                 365

Gly Thr Ile Glu Asp Thr Ser Gly Ala Phe Ser Gly Leu Asp Ser Leu
370                 375                 380

Ser Lys Leu Thr Leu Phe Gly Asn Lys Ile Lys Ser Val Ala Lys Arg
385                 390                 395                 400

Ala Phe Ser Gly Leu Glu Gly Leu Glu His Leu Asn Leu Gly Gly Asn
                405                 410                 415

Ala Ile Arg Ser Val Gln Phe Asp Ala Phe Val Lys Met Lys Asn Leu
                420                 425                 430

Lys Glu Leu His Ile Ser Ser Asp Ser Phe Leu Cys Asp Cys Gln Leu
            435                 440                 445

Lys Trp Leu Pro Pro Trp Leu Ile Gly Arg Met Leu Gln Ala Phe Val
450                 455                 460

Thr Ala Thr Cys Ala His Pro Glu Ser Leu Lys Gly Gln Ser Ile Phe
465                 470                 475                 480
```

```
Ser Val Pro Pro Glu Ser Phe Cys Asp Asp Phe Leu Lys Pro Gln
            485                 490                 495

Ile Ile Thr Gln Pro Glu Thr Thr Met Ala Met Val Gly Lys Asp Ile
            500                 505                 510

Arg Phe Thr Cys Ser Ala Ala Ser Ser Ser Ser Pro Met Thr Phe
            515                 520                 525

Ala Trp Lys Lys Asp Asn Glu Val Leu Thr Asn Ala Asp Met Glu Asn
    530                 535                 540

Phe Val His Val His Ala Gln Asp Gly Glu Val Met Glu Tyr Thr Thr
545                 550                 555                 560

Ile Leu His Leu Arg Gln Val Thr Phe Gly His Glu Gly Arg Tyr Gln
            565                 570                 575

Cys Val Ile Thr Asn His Phe Gly Ser Thr Tyr Ser His Lys Ala Arg
            580                 585                 590

Leu Thr Val Asn Val Leu Pro Ser Phe Thr Lys Thr Pro His Asp Ile
            595                 600                 605

Thr Ile Arg Thr Thr Thr Met Ala Arg Leu Glu Cys Ala Ala Thr Gly
    610                 615                 620

His Pro Asn Pro Gln Ile Ala Trp Gln Lys Asp Gly Gly Thr Asp Phe
625                 630                 635                 640

Pro Ala Ala Arg Glu Arg Arg Met His Val Met Pro Asp Asp Val
            645                 650                 655

Phe Phe Ile Thr Asp Val Lys Ile Asp Asp Ala Gly Val Tyr Ser Cys
            660                 665                 670

Thr Ala Gln Asn Ser Ala Gly Ser Ile Ser Ala Asn Ala Thr Leu Thr
            675                 680                 685

Val Leu Glu Thr Pro Ser Leu Val Val Pro Leu Glu Asp Arg Val Val
    690                 695                 700

Ser Val Gly Glu Thr Val Ala Leu Gln Cys Lys Ala Thr Gly Asn Pro
705                 710                 715                 720

Pro Pro Arg Ile Thr Trp Phe Lys Gly Asp Arg Pro Leu Ser Leu Thr
            725                 730                 735

Glu Arg His His Leu Thr Pro Asp Asn Gln Leu Leu Val Val Gln Asn
            740                 745                 750

Val Val Ala Glu Asp Ala Gly Arg Tyr Thr Cys Glu Met Ser Asn Thr
            755                 760                 765

Leu Gly Thr Glu Arg Ala His Ser Gln Leu Ser Val Leu Pro Ala Ala
    770                 775                 780

Gly Cys Arg Lys Asp Gly Thr Thr Val Gly Ile Phe Thr Ile Ala Val
785                 790                 795                 800

Val Ser Ser Ile Val Leu Thr Ser Leu Val Trp Val Cys Ile Ile Tyr
            805                 810                 815

Gln Thr Arg Lys Lys Ser Glu Glu Tyr Ser Val Thr Asn Thr Asp Glu
            820                 825                 830

Thr Val Val Pro Pro Asp Val Pro Ser Tyr Leu Ser Ser Gln Gly Thr
            835                 840                 845

Leu Ser Asp Arg Gln Glu Thr Val Val Arg Thr Glu Gly Gly Pro Gln
    850                 855                 860

Ala Asn Gly His Ile Glu Ser Asn Gly Val Cys Pro Arg Asp Ala Ser
865                 870                 875                 880

His Phe Pro Glu Pro Asp Thr His Ser Val Ala Cys Arg Gln Pro Lys
            885                 890                 895
```

```
Leu Cys Ala Gly Ser Ala Tyr His Lys Glu Pro Trp Lys Ala Met Glu
                900                 905                 910
Lys Ala Glu Gly Thr Pro Gly Pro His Lys Met Glu His Gly Gly Arg
            915                 920                 925
Val Val Cys Ser Asp Cys Asn Thr Glu Val Asp Cys Tyr Ser Arg Gly
        930                 935                 940
Gln Ala Phe His Pro Gln Pro Val Ser Arg Asp Ser Ala Gln Pro Ser
945                 950                 955                 960
Ala Pro Asn Gly Pro Glu Pro Gly Gly Ser Asp Gln Glu His Ser Pro
                965                 970                 975
His His Gln Cys Ser Arg Thr Ala Ala Gly Ser Cys Pro Glu Cys Gln
            980                 985                 990
Gly Ser Leu Tyr Pro Ser Asn His Asp Arg Met Leu Thr Ala Val Lys
        995                 1000                1005
Lys Lys Pro Met Ala Ser Leu Asp Gly Lys Gly Asp Ser Ser Trp Thr
    1010                1015                1020
Leu Ala Arg Leu Tyr His Pro Asp Ser Thr Glu Leu Gln Pro Ala Ser
1025                1030                1035                1040
Ser Leu Thr Ser Gly Ser Pro Glu Arg Ala Glu Ala Gln Tyr Leu Leu
                1045                1050                1055
Val Ser Asn Gly His Leu Pro Lys Ala Cys Asp Ala Ser Pro Glu Ser
            1060                1065                1070
Thr Pro Leu Thr Gly Gln Leu Pro Gly Lys Gln Arg Val Pro Leu Leu
        1075                1080                1085
Leu Ala Pro Lys Ser
    1090

<210> SEQ ID NO 12
<211> LENGTH: 3282
<212> TYPE: DNA
<213> ORGANISM: Homo sapiens

<400> SEQUENCE: 12
atggcgcggc cggtccgggg agggctcggg gccccgcgcc gctcgccttg ccttctcctt      60
ctctggctgc ttttgcttcg gctggagccg gtgaccgccg cggccggccc gcgggcgccc     120
tgcgcggccg cctgcacttg cgctggggac tcgctggact gcggtgggcg cgggctggct     180
gcgttgcccg gggacctgcc ctcctggacg cggagcctaa acctgagtta caacaaactc     240
tctgagattg accctgctgg ttttgaggac ttgccgaacc tacaggaagt gtacctcaat     300
aataatgagt tgacagcggt accatccctg ggcgctgctt catcacatgt cgtctctctc     360
tttctgcagc acaacaagat tcgcagcgtg gaggggagcc agctgaaggc ctaccttttcc     420 ttagaagtgt tagatctgag tttgaacaac atcacggaag tgcggaacac ctgctttcca     480
cacggaccgc ctataaagga gctcaacctg gcaggcaatc ggattggcac cctggagttg     540
ggagcatttg atggtctgtc acggtcgctg ctaactcttc gcctgagcaa aaacaggatc     600
acccagcttc ctgtaagagc attcaagcta cccaggctga cacaactgga cctcaatcgg     660
aacaggattc ggctgataga gggcctcacc ttccaggggc tcaacagctt ggaggtgctg     720
aagcttcagc gaaacaacat cagcaaactg acagatgggg ccttctgggg actgtccaag     780
atgcatgtgc tgcacctgga gtacaacagc ctggtagaag tgaacagcgg ctcgctctac     840
ggcctcacgg ccctgcatca gctccacctc agcaacaatt ccatcgctcg cattcaccgc     900
aagggctgga gcttctgcca gaagctgcat gagttggtcc tgtccttcaa caacctgaca     960
```

-continued

```
cggctggacg aggagagcct ggccgagctg agcagcctga gtgtcctgcg tctcagccac      1020
aattccatca gccacattgc ggagggtgcc ttcaagggac tcaggagcct gcgagtcttg      1080
gatctggacc ataacgagat tcgggcaca atagaggaca cgagcggcgc cttctcaggg      1140
ctcgacagcc tcagcaagct gactctgttt ggaaacaaga tcaagtctgt ggctaagaga      1200
gcattctcgg ggctggaagg cctggagcac ctgaaccttg agggaatgc gatcagatct       1260
gtccagtttg atgcctttgt gaagatgaag aatcttaaag agctccatat cagcagcgac      1320
agcttcctgt gtgactgcca gctgaagtgg ctgcccccgt ggctaattgg caggatgctg      1380
caggcctttg tgacagccac ctgtgcccac ccagaatcac tgaagggtca gagcattttc      1440
tctgtgccac cagagagttt cgtgtgcgat gacttcctga agccacagat catcacccag      1500
ccagaaacca ccatggctat ggtgggcaag acatccggt ttacatgctc agcagccagc      1560
agcagcagct cccccatgac cttttgcctgg aagaaagaca atgaagtcct gaccaatgca      1620
gacatggaga ctttgtcca cgtccacgcg caggacgggg aagtgatgga gtacaccacc      1680
atcctgcacc tccgtcaggt cactttcggg cacgagggcc gctaccaatg tgtcatcacc      1740
aaccactttg gctccaccta ttcacataag gccaggctca ccgtgaatgt gttgccatca      1800
ttcaccaaaa cgccccacga cataaccatc cggaccacca ccatggcccg cctcgaatgt      1860
gctgccacag gtcacccaaa ccctcagatt gcctggcaga aggatggagg cacggattc       1920
cccgctgccc gtgagcgacg catgcatgtc atgccggatg acgacgtgtt tttcatcact      1980
gatgtgaaaa tagatgacgc aggggtttac agctgtactg ctcagaactc agccggttct      2040
atttcagcta atgccaccct gactgtccta gagaccccat ccttggtggt ccccttggaa      2100
gaccgtgtgg tatctgtggg agaaacagtg gccctccaat gcaaagccac ggggaaccct      2160
ccgccccgca tcacctggtt caaggggac cgccgctga cctcactga gcggcaccac        2220
ttgaccctg acaaccagct cctggtggtt cagaacgtgg tggcagagga tgcgggccga      2280
tatacctgtg agatgtccaa caccctgggc acggagcgag ctcacagcca gctgagcgtc      2340
ctgcccgcag caggctgcag gaaggatggg accacggtag gcatcttcac cattgctgtc      2400
gtgagcagca tcgtcctgac gtcactggtc tgggtgtgca tcatctacca gaccaggaag      2460
aagagtgaag agtacagtgt caccaacaca gatgaaaccg tcgtgccacc agatgttcca      2520
agctacctct cttctcaggg gacccttct gaccgacaag aaaccgtggt caggaccgag      2580
ggtggccctc aggccaatgg gcacattgag agcaatggtg tgtgtccaag agatgcaagc      2640
cactttccag agcccgacac tcacagcgtt gcctgcaggc agccaaagct ctgtgctggg      2700
tctgcgtatc acaaagagcc gtggaaagcg atggagaaag ctgaagggac acctgggcca      2760
cataagatgg aacacggtgg ccgggtcgta tgcagtgact gcaacaccga agtggactgt      2820
tactccaggg gacaagcctt ccacccccag cctgtgtcca gagacagcgc acagccaagt      2880
gcgccaaatg gcccggagcc gggtgggagt gaccaagagc attctccaca tcaccagtgc      2940
agcaggactg ccgctgggtc ctgccccgag tgccaagggc gctctaccc cagtaaccac       3000
gatagaatgc tgacggctgt gaagaaaaag ccaatggcat ctctagatgg gaaaggggat      3060
tcttcctgga ctttagcaag gttgtatcac ccggactcca cagagctaca gcctgcatct      3120
tcattaactt caggcagtcc agagcgcgcg gaagcccagt acttgcttgt ttccaatggc      3180
cacctcccca agcatgtgat cgccagtccc gagtccacgc cactgacagg acagctcccc      3240
gggaaacaga gggtgccact gctgttggca ccaaaaagct ag                         3282
```

-continued

<210> SEQ ID NO 13
<211> LENGTH: 758
<212> TYPE: PRT
<213> ORGANISM: Homo sapiens

<400> SEQUENCE: 13

Ala Gly Pro Arg Ala Pro Cys Ala Ala Cys Thr Cys Ala Gly Asp
1               5                   10                  15

Ser Leu Asp Cys Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

-continued

```
Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
            405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
            435                 440                 445

Pro Pro Glu Ser Phe Val Cys Asp Asp Phe Leu Lys Pro Gln Ile Ile
            450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Pro Met Thr Phe Ala Trp
            485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
            515                 520                 525

His Leu Arg Gln Val Thr Phe Gly His Glu Gly Arg Tyr Gln Cys Val
            530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
            565                 570                 575

Arg Thr Thr Thr Met Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
            595                 600                 605

Ala Arg Glu Arg Arg Met His Val Met Pro Asp Asp Asp Val Phe Phe
            610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
            645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
            675                 680                 685

Arg Ile Thr Trp Phe Lys Gly Asp Arg Pro Leu Ser Leu Thr Glu Arg
            690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
            725                 730                 735

Thr Glu Arg Ala His Ser Gln Leu Ser Val Leu Pro Ala Ala Gly Cys
            740                 745                 750

Arg Lys Asp Gly Thr Thr
            755
```

US 11,932,686 B2

USE OF REGULATORY T CELL-SPECIFIC SURFACE PROTEIN LRIG-1

PRIORITY

This application is a continuation application of U.S. Ser. No. 16/233,738, filed on Dec. 27, 2018, which is a continuation application of U.S. Ser. No. 14/427,421, filed on Mar. 11, 2015, which is a 371 National Stage Application that claims priority to International Patent Application No. PCT/KR2012/00532, filed on Jan. 20, 2012, which claims the benefit of KR10-2011-0007022, filed on Jan. 24, 2011, all of which are incorporated in their entirety by reference herein.

TECHNICAL FIELD

The present invention relates to a novel use of regulatory T cell-specific surface protein Lrig-1.

BACKGROUND ART

The inflammatory and immune responses are a very important biological phenomenon that protects the body from outside harmful substances (bacteria, virus) using various inflammatory cells and immune cells, among which the T cells play an important role like the brain that makes an overall regulation for the inflammatory and immune responses. It has been known that the human with a variety of different genetic and environmental factors may naturally produce excessive inflammatory and immune responses and that the internal risk factors (high cholesterol, blood sugar, etc.) threatening the health and safety of a living body may cause chronic inflammation and immune hypersensitivity reactions, which lead to autoimmune diseases (asthma, atopy, rheumatoid arthritis, Crohn's disease, MS) and chronic inflammatory diseases (myocardial infarction, diabetes, degenerative cerebrovascular diseases), finally leading to the death.

The regulatory T cell (Treg), one subset in T cells of the body, plays an important role to naturally prevent the occurrence of excessive inflammation and immune responses, but if autoimmune diseases and chronic inflammatory diseases are occurred, the function and number of the regulatory T cells have been known to be rather significantly reduced. Therefore, for patients with immune diseases and inflammatory diseases, generating a lot of the regulatory T cells is the most important and natural therapy. Further, in the recent studies, cancer cells have been known to inhibit the natural immunity of cancer cells in a living body by increasing the number and function of the regulatory T-cells (Treg) around them, thus allowing the occurrence, progression and metastasis of cancers. Until now, a few regulatory T cell (Treg)-specific genes and proteins have been developed and published.

In studies to date, the Treg has been known to express a high level of CD25. CD25 constitutes heterotrimer IL-2 receptor with α,β,γ-chains. This has been known to have more than 100 fold affinity to IL-2 as compared to β, γ-chain heterodimer IL-2 receptors existed in conventional non-contacted T cells. Through competition for IL-2 greatly involved in T cell proliferation, the proliferation of non-contacted T cells is inhibited to control the immune response. IL-2 has been used as labeled materials for the regulatory T cells up to now, but IL-2 receptor with a high level of homologous relation is expressed in a high level upon activation of the different types of T cells, and thus it is difficult to become definite labeling materials.

It has been known that since Treg express CTLA4, they combine with CD80 or CD86 expressed in the other immune T cells or antigen-presenting cells to thereby inhibit the activation thereof. However, recently, when the different types of immune T cells such as T helper 1 or T helper 2 cells are also activated and, after passing a certain time, the expression of IL-2 is reduced, it has been reported that the expression of CTLA4 is increased. It has been also known that CTLA4 are also not the material specifically expressed in Treg.

Therefore, in order to differentiate the regulatory T cells, alternative labeling materials such as low expression levels of CD62L, CD38, CD103, GITR and CD45RB have been proposed. As it has been discovered that, among them, the transcription factor, Foxp3 (Forkhead box 3), plays a decisive role in the differentiation and activity of natural CD4+ regulatory T cells, this has been known to be the most effective labeling material. However, as the expression of Foxp3 in CD4+ IL-10+ Tr1 cells which exhibit immunoregulatory functions in the peripheral has been found to be not essential, the potential as the regulatory T cell (Treg)-specific markers of Foxp3 has been gradually diluted (see, IL-35-mediated induction of a potent regulatory T cell population, Laren W Collison et al., Vol. 11, Nature Immunology, 1093-1952, 2010). Furthermore, the technology of controlling the function or expression of Foxp3 to thereby control the function of the regulatory T cells (Treg) has not been known up to now. Because of molecular biological characteristics that Foxp3 is a transcription factor, it is not possible to use Foxp3 as a marker for the development of medicines for treating diseases and the separation of Treg cells using Foxp3.

On the other hand, LRIG1 (leucine-rich and immunoglobulin-like domains 1) protein is a transmembrane protein, and LRIG1 gene is highly expressed in normal skin and expressed in basal and follicular cells to regulate the proliferation of epithelial stem cells. Therefore, the LRIG is important in maintaining the homeostasis of the epidermis and the absence thereof may develop psoriasis or skin cancer. The gene family of LRIG is present in three types, i.e., LRIG1, LRIG2 and LRIG3. The amino acid sequence homology between these families is more than 60% (for LRIG1 and LRIG2) and more than 40% (for LRIG1 and LRIG3). The amino acid sequence of important functional domain maintains substantially 100%. As such, LRIG2 and LRIG3 are also anticipated to have a lot of functional similarity. Further, as shown in Example 10 of the present invention, LRIG1 is specifically highly expressed even in the regulatory T cells of the human. In particular, the expression has been shown to increase in the activated or proliferated regulatory T cells. It has been reported that cutting off the chromosome 3p14.3 part at which LRIG1 is positioned is highly likely to develop into cancer cells. Actually, it has been identified that the expression of LRIG1 is greatly reduced in renal cell carcinoma and cutaneous squamous cell carcinoma. Currently, LRIG1 induces the ubiquitination of EGFR (Epidermal Growth Factor Receptor) via c-Cbl to degrade a protein and so blocks the signal transduction by phosphorylation of MAPK and AKT which is present in the lower part and involved in cell proliferation and increases the secretion of caspase-8, thus leading to apoptosis. In this regard, the potential as a cancer inhibitor has been suggested.

The present inventor has conducted numerous researches and experiments in order to find out genes or proteins specifically expressed in the regulatory T cells, and discovered that Lrig-1 is specifically expressed in the regulatory T cells through bioinformatics approaches called microarray, proteomics and functional gene network and that the expression is important in the function, differentiation and growth of the regulatory T cells (Treg). The present invention has been completed on the basis of such discovery.

DISCLOSURE

Technical Problem

The present invention provides a method for screening immunosuppressive agents or immune activators which comprises the steps of (a) contacting an analyzing sample to a regulatory T cell including Lrig (leucine-rich repeats and immunoglobulin-like domains) protein; (b) measuring the amount or activity of the protein; and (c) determining that the sample is the immunosuppressive agents or the immune activators when the amount or activity of the protein is measured to be down- or up-regulated.

The present invention also provides a composition for treating immune-related diseases comprising Lrig 1 protein.

Technical Solution

In one embodiment of the present invention, there is provided a method for screening immunosuppressive agents or immune activators which comprises the steps of (a) contacting an analyzing sample to a regulatory T cell including Lrig (leucine-rich repeats and immunoglobulin-like domains) protein; (b) measuring the amount or activity of the protein; and (c) determining that the sample is the immunosuppressive agents or the immune activators when the amount or activity of the protein is measured to be down- or up-regulated. The Lrig protein may be any one selected from the group consisting of Lrig 1, Lrig 2 or Lrig 3. Further, the Lrig protein is set forth in SEQ ID NO: 11.

In one embodiment of the present invention, there is provided a method for screening immunosuppressive agents or immune activators which comprises the steps of (a) contacting an analyzing sample to a regulatory T cell (Treg) including LRIG gene; (b) measuring the expression level of the gene; and (c) determining that the sample is the immunosuppressive agents or the immune activators when the expression level of the gene is measured to be down- or up-regulated. The LRIG gene may be a nucleotide encoding SEQ ID NO: 11. Further, the LRIG gene may be a nucleotide as set forth in SEQ ID NO: 12.

In another embodiment of the present invention, there is provided a method for screening immunosuppressive agents or immune activators for combination administration which comprises (a) the first step of contacting the immunosuppressive agents or the immune activators to cells including Lrig 1 protein as set forth in SEQ ID NO: 11 and then measuring the amount or activity of the protein; (b) the second step of contacting an analyzing sample, the immunosuppressive agents or the immune activators to cells including Lrig 1 protein as set forth in SEQ ID NO: 11 and then measuring the amount or activity of the protein; and (c) the step of comparing the measurement values of the first and second steps and then determining that the sample is the immunosuppressive agents or the immune activators for combination administration when the measurement value of the second step is down- or up-regulated as compared to the measurement value of the first step. The immunosuppressive agents may be any one selected from the group consisting of Glucocorticoids, Cyclophosphamide, Cyclosporin, Tacrolimus, Rapamycin, Type IV PDE inhibitors, p38 kinase inhibitors, Azathioprine, mycophenolate mofetil, Mizoribin, Methotrexate, Leflunomid, Brequina and Methotrexate.

In one embodiment of the present invention, there is provided a method for screening immunosuppressive agents or immune activators for combination administration which comprises (a) the first step of contacting the immunosuppressive agents or the immune activators to cells including LRIG1 gene as set forth in SEQ ID NO: 12 and then measuring the expression level of the gene; (b) the second step of contacting an analyzing sample, the immunosuppressive agents or the immune activators to cells including LRIG1 gene as set forth in SEQ ID NO: 12 and measuring the expression level of the gene; and (c) comparing the measurement values of the first and second steps and determining that the sample is the immunosuppressive agents or the immune activators for combination administration when the measurement value of the second step is down- or up-regulated as compared to the measurement value of the first step. The immunosuppressive agent may be any one selected from the group consisting of Glucocorticoids, Cyclophosphamide, Cyclosporin, Tacrolimus, Rapamycin, Type IV PDE inhibitors, p38 kinase inhibitors, Azathioprine, mycophenolate mofetil, Mizoribin, Methotrexate, Leflunomid, Brequina and Methotrexate.

In one embodiment of the present invention, there is provided an immunosuppressive agent comprising, as an active ingredient, an antisense having a sequence complementary to the nucleotide sequence as set forth in SEQ ID NO: 12 or siRNA (small interference RNA) oligonucleotide. The siRNA may be any one of siRNA as set forth in SEQ ID NO: 7, 8, 9, or 10. The immunosuppressive agents are characterized by treating any one disease selected from the groups consisting of autoimmune diseases, graft versus host diseases, organ transplant rejection, asthma, atopy, acute and chronic inflammatory diseases, cardiovascular diseases and cognitive disorders.

In one embodiment of the present invention, there is provided a kit for diagnosis of immune-related diseases comprising all or part of the antibody specifically binding to Lrig1 protein. The Lrig1 protein may be set forth in SEQ ID NO: 11. Also, the immune-related diseases may be any one selected from the group consisting of an autoimmune disease, graft versus host diseases, organ transplant rejection, asthma, atopy, acute and chronic inflammatory diseases, cardiovascular diseases and cognitive disorders.

In one embodiment of the present invention, there is provided a kit for diagnosis of immune-related diseases comprising all or part of the antibody specifically binding to a cell membrane surface protein of Lrig1 protein. The cell membrane surface protein of Lrig1 protein may be set forth in SEQ ID NO: 13. Also, the immune-related diseases may be any one selected from the group consisting of autoimmune diseases, graft versus host diseases, organ transplant rejection, asthma, atopy, acute and chronic inflammatory diseases, cardiovascular diseases and cognitive disorders.

In one embodiment of the present invention, there is provided a composition for treating immune-related diseases comprising Lrig1 protein. The Lrig1 protein may be set forth in SEQ ID NO: 11. Also, the immune-related diseases may be any one selected from the group consisting of autoimmune diseases, graft versus host diseases, organ transplant rejection, asthma, atopy, acute and chronic inflammatory diseases, cardiovascular diseases and cognitive disorders.

In one embodiment of the present invention, there is provided a composition for treating immune-related diseases comprising a cell membrane surface protein of Lrig1 protein or a protein including all or part of the antibody specifically binding thereto. The cell membrane surface protein of Lrig1 protein may be set forth in SEQ ID NO: 13. Also, the immune-related disease may be any one selected from the group consisting of autoimmune diseases, graft versus host diseases, organ transplant rejection, asthma, atopic dermatitis, acute and chronic inflammatory diseases, cardiovascular diseases and cognitive disorders.

In one embodiment of the present invention, there is provided a composition for anti-cancer treatment comprising Lrig1 protein. The Lrig1 protein may be set forth in SEQ ID NO: 11.

In one embodiment of the present invention, there is provided a composition for anti-cancer treatment comprising a cell membrane surface protein of Lrig1 protein or a protein including all or part of antibody specifically binding thereto. The cell membrane surface protein of Lrig1 protein may be set forth in SEQ ID NO: 13.

In one embodiment of the present invention, there is provided a composition for promoting vaccination comprising Lrig1 protein. The Lrig1 protein may be set forth in SEQ ID NO: 11.

In one embodiment of the present invention, there is provided a composition for promoting vaccination comprising a protein including a cell membrane surface protein of Lrig1 protein or all or part of antibody specifically binding thereto. The cell membrane surface protein of the Lrig1 protein may be set forth in SEQ ID NO: 13.

In one embodiment of the present invention, there is provided a method for screening regulatory T cells overexpressing Lrig1 protein; and a method for treating immune-related diseases comprising administering an effective amount of the screened regulatory T cells to a subject with immune-related diseases. The immune-related diseases may be any one selected from the group consisting of autoimmune diseases, graft versus host diseases, organ transplant rejection, asthma, atopic dermatitis, acute and chronic inflammatory diseases, cardiovascular diseases and cognitive disorders.

In one embodiment of the present invention, there is provided a method for treating an immune-related disease comprising administering an effective amount of a Lrig1 protein, or a protein comprising a cell membrane surface protein of the Lrig1 protein, or a composition comprising all or part of the antibody specifically binding thereto to a subject with the immune-related diseases. The Lrig1 protein may be set forth in SEQ ID NO: 11. The cell membrane surface protein of Lrig1 protein may be set forth in SEQ ID NO: 13. The immune-related diseases may be any one selected from the group consisting of autoimmune diseases, graft versus host diseases, organ transplant rejection, asthma, atopic dermatitis, acute and chronic inflammatory diseases, cardiovascular diseases and cognitive disorders.

In one embodiment of the present invention, there is provided a method for screening regulatory T cells overexpressing Lrig1 protein; and a method for treating caners comprising administering an effective amount of the screened regulatory T cells to a subject with the cancers.

In one embodiment of the present invention, there is provided a method for treating cancers comprising administering an effective amount of a Lrig1 protein, or a protein comprising a cell membrane surface protein of Lrig1 protein, or a composition including all or part of the antibody specifically binding thereto to a subject with the cancers. The Lrig1 protein may be set forth in SEQ ID NO: 11. The cell membrane surface protein of the Lrig1 protein may be set forth in SEQ ID NO: 13.

In one embodiment of the present invention, there is provided a composition for promoting vaccination comprising administering a Lrig1 protein, or a protein comprising a cell membrane surface protein of the Lrig1 protein to a subject. The Lrig1 protein may be set forth in SEQ ID NO: 11. The cell membrane surface protein of Lrig1 protein may be set forth in SEQ ID NO: 13.

The term "immune-related disease" as used herein refers to diseases induced by excessive activation or inhibition of various immune cells and inflammatory cells, for example, but is not limited to, autoimmune diseases, graft versus host diseases, transplant rejection, asthma, atopy, acute and chronic inflammatory diseases, cardiovascular disease and cognitive disorders.

In the present invention, Lrig1 (leucine-rich and immunoglobulin-like domains 1) is a transmembrane protein consisting of 1091 amino acids, and consists of leucine repeat sequence (leucine-rich repeat (LRR)) of the extracellular or lumen side and three immune antibody-like domain (immunoglobulin-like domains), cell transmembrane sequences and cytoplasmic tail part. The LRIG gene family consists of LRIG1, LRIG2 and LRIG3, and amino acids between them are very conservative.

In the present invention, "siRNA (small interfering RNA)" are a class of double-stranded RNA duplex with short 19-30 ribonucleic acid chains, which exhibits the effects of inhibiting only the expression of a certain gene without non-specific inhibition if introduced within cells. The mechanism of action of siRNA has been known that siRNA combines with RISC (RNA-induced silencing complex) within cells, the sense strand of genes corresponding to mRNA is cut off and the antisense stand complementary to the sense strand is present as a complex with RISC and then combined with mRNA having the complementary base sequence, that is, mRNA of the target gene to decompose them, thereby inhibiting the expression of the gene.

In the present invention, "shRNA (short hairpin RNA)" means that oligo DNA connecting 3-10 base linkers are synthesized between the sense and complementary nonsense of target gene siRNA sequences and then cloned to plasmid vector, or shRNA is inserted and expressed into retrovirus such as lentivirus and adenovirus to thereby make shRNA of hairpin structure with loop, which is converted into siRNA via Dicer within cells, thus exhibiting RNAi effects. shRNA has advantages that it has RNAi effects for a relatively long-term. siRNA of the present invention may be a chemically modified form to prevent the rapid degradation by in vivo nuclease. Since siRNA has a double helix structure, which is a relatively stable structure as compared with ribonucleic acids or antisense oligonucleotides having a single helix structure, but it is rapidly degraded by the in vivo nuclease. Therefore, the siRNA can reduce the degradation speed through a chemical modification. The method for chemically modifying siRNA into stable and resistant forms so that siRNA is not easily degraded have been well known to a person skilled in the art.

The most common method used for the chemical modification of siRNA is the method for modification of boranophosphate or phosphorothioate. These materials stably form a connection between the nucleosides of siRNA, thus imparting a resistance to nucleic acid decomposition. The ribonucleic acid modified with boranophosphate has characteristic that the degradation of the nucleic acid is not well made. However, this ribonucleic acid is not made by a chemical reaction, but synthesized only by the manner wherein boranophosphate enters into the ribonucleic acid by in vitro transcription reaction.

The method for modification of boranophosphate is relatively easy, but has a drawback which is difficult to modify at a particular position. On the other hand, the method for modification of phosphorothioate has an advantage that can introduce a sulfur atom in a desired portion. However, a severe degree of phosphothioation may appear problems, for example, decrease of efficacy, toxicity, non-specific RISC (RNAinduced silencing complex) formation, etc.

Therefore, recently, in addition to the above two methods, the method of conducting the chemical modification only at the end position (the 3' terminal exceeding part) to impart resistance to the nuclease is more preferred. It is also known that, although ribose ring is chemically modified, resistance to the nuclease become strong. In particular, variations of the ribose 2'-position in the original cells will stabilize siRNA. However, when the methyl group exactly enters this position, the stability is increased, whereas too many methyl groups may cause problems, for example, loss of RNA-mediated interference. The purpose of such chemical modification is to increase the efficacy and the pharmacokinetic residence time in vivo (see Mark et al., Molecular Therapy, 13: 644-670, 2006). In addition to the chemical modification, in order to increase the delivery efficiency within cells of siRNA, a safe and efficient delivery system is required. To this end, siRNA of the present invention may be included in the pharmaceutical composition for the treatment of cancers in a complex form with nucleic acid delivery system.

The nucleic acid delivery system for delivering a nucleic acid substance into cells may be greatly divided into a viral vector and a non-viral vector. The most widely used system is a viral vector because the delivery efficiency is high and the time of duration is long. Among various viral vectors, retroviral vector, adenoviral vector, adeno-associated viral vector and the like are mainly used. These viral vectors are efficient in view of the cell delivery of the ribonucleic acid, but it has a number of problems in view of safety such as a recombinant into virus having activity in a living body, induction of the immune response, random insert into host chromosome, and the like. In contrast, nonviral vectors have the advantages over the viral vectors, that is, the immune response to the toxicity is low, repeated administration is possible, formation of a complex with RNA is simple, and mass production is easy. Also, a specific ligand at a disease cell or a tissue site is conjugated to a non-viral vector, thus allowing for a long-term cell selective nucleic acid delivery. As the non-viral vectors, a variety of formulations, such as micelles, emulsions, nanoparticles, including liposomes and cationic polymers, can be used. The nucleic acid delivery system can significantly enhance the transport efficiency of the desired nucleic acid in animal cells and the nucleic acid delivery can be made even to any animal cell in accordance with the intended use of the nucleic acid to be delivered.

The monoclonal antibodies to the protein of the present invention may be produced and used by a conventional method for producing monoclonal antibodies in the technical field to which the present invention pertains. Typically, the commercially available antibodies can be used. Monoclonal antibodies to the proteins can be quantitatively analyzed by conducting a color reaction using the secondary antibodies and substrates thereof conjugated with enzymes such as alkaline phosphatase (AP) or horseradish peroxidase (HRP). Alternatively, it can be quantitatively analyzed using those where AP or HRP enzymes are conjugated directly to the monoclonal antibodies to the proteins. In addition, the polyclonal antibodies which recognize the protein in place of the monoclonal antibodies can be used. The polyclonal antibodies can be produced and used by a conventional method for producing antiserum in the technical field to which the present invention pertains.

The protein of the present invention comprises a fusion protein, which is expressed by combining or linking at least two different proteins through a method of genetic engineering, and which has two or more functions. In particular, in the case of an antibody, the multi-functional antibody can be produced by replacing Fab region or Fc region with other protein.

In the screening method of the present invention, the reaction between the composition comprising the protein and the testing substances can be identified using a conventional method which is used to identify the reaction between protein-protein and protein-compound. For example, the method of measuring the activity after the reaction of the protein and the testing substance, yeast two-hybrid and the like can be used.

Search of phage-displayed peptide clone binding to the protein, high throughput screening (HTS) using natural products and chemical libraries, drug hit HTS, cell-based screening or screening method using DNA array can be used. In this case, the composition of the present invention may comprise, in addition to the protein, a buffer or reaction solution to stably maintain a structure or physiological activity of the protein. In addition, the compositions of the present invention may comprise, for the in vivo experiments, cells expressing the protein, or cells containing a plasmid expressing the protein under a promoter capable of controlling the transcription ratio.

In the screening method of the present invention, the testing substances used here may include individual nucleic acids, proteins, other extracts or natural products, compounds, etc., which are assumed to have a potential as a cancer metastasis inhibitor according to the conventional screening manner or randomly selected. Further, it may include the testing substance which is obtained through the screening method of the present invention and which exhibits activities to promote the gene expression or enhance the function of the protein, and inversely the testing substance showing an activity to inhibit the expression of the gene or inhibit the function of the protein. The former may be a candidate immunosuppressive agent by developing an inhibitor into the testing substance, and the latter may be a candidate immunosuppressive agent. Such candidate immunosuppressive agent acts as a leading compound in the subsequent development process of the immunosuppressive agent. A new immunosuppressive agent can be developed by transforming and optimizing the structure so that the leading compound can exhibit the suppressive effect of the gene or protein expressed therefrom.

The immune related diseases can be treated using the protein or the antibody of the present invention. That is, in the case of autoimmune diseases, when ERK is activated with the selectively produced ERK activator, the resistant dendritic cells are activated, thereby proliferating the regulatory T cell and increasing the number of the proliferation, the result of which confirms the effect of RA treatment (see Arthritis Rheum. 2011 January; 63 (1):84-95, "selective ERK activation differentiates mouse and human tolerogenic dendritic cells, expands antigen-specific regulatory T cells, and suppresses experimental inflammatory arthritis"). When treated to mice which induced RA by injection of type II collagen using Anti-CD3, the numbers of CD4+CD25+Foxp3+Regulatory T cells and CD8+CD25+Foxp3+Regulatory T cells were greatly increased, and so it can be used in the treatment of RA (see Arthritis Rheum. 2010 January; 62 (1): 171-8, "ANTI-CD3 therapy expands the numbers of CD4+ and CD8+Treg cells and induces sustained amelioration of collagen-induced arthritis"). When TCR BV8S2 CDR2 peptide found to do an immunosuppressive action was treated to the non-transgenic C57BL/6 EAE model, EAE was greatly suppressed. This is because the immune action was controlled as the number of regulatory T cells rapidly increased, thereby improving the symptom (see Immunology. 2012 February; 135 (2):168-79, "Regulatory T cells play a role in T-cell receptor CDR2 peptide regulation of experimental autoimmune encephalomyelitis"). In the case of patients suffering from IBD, the regulatory T cells become self-apoptosis to cause damage to the immune regulatory system. Therefore, it has been observed that in order to suppress this, the apoptosis of regulatory T cells is increased in chronic inflammatory bowel diseases by anti-TNF-alpha treatment (see Gut. 2011 October; 60 (10):1345-53. Epub 2011 Apr. 1. "Apoptosis of regulatory T lymphocytes is increased in chronic inflammatory bowel disease and reversed by anti-TNFα treatment"). When 12-O-tetradecanoylphorbol 13-acetate to induce psoriasis was treated to the mice prepared by conducing knockout (Pglyrp2), it was confirmed to induce the more severe inflammation response than the wild type mice.

The mechanism that Pglyrp2 controls the inflammatory response was confirmed to limit Th17 responses and, at the same time, promote and activate the regulatory T cells (see J Immunol. 2011 Dec. 1; 187 (11):5813-23. Epub 2011 Nov. 2, "Peptidoglycan recognition protein Pglyrp2 See protects mice from psoriasis-like skin inflammation by promoting regulatory T cells and limiting Th17 responses").

On the other hand, it has been found that the treatment was possible by reducing the number of CD4+T cells in colorectal cancer (CRC), but the treatment was not made. The reason is that the regulatory T cells were over-expressed, thereby suppressing the immune function to remove the tumor cells. In order to confirm whether CRC patient is the same, the amount of Foxp3 was confirmed. The result showed that the regulatory T cells were enriched in CRC patients (see Gut. 2011 Dec. 29, "Suppression of tumour-specific CD4+ T cells by regulatory T cells is associated with progression of human colorectal cancer").

In addition, using Alloreactive regulatory T cells, the possibility of conducting the organ transplant without continuous immunosuppression which is the biggest problem of an organ transplant has been suggested (see Eur J Immunol 2011 March; 41 (3): 726-38 doi:10.1002/eji.201040509. Epub 2011 Jan. 17, "Induction of transplantation tolerance converts potential effector T cells into graft-protective regulatory T cells").

The blood vessel where the regulatory T cells in cardiac fibrosis was treated with adoptive transfer was significantly improved (see J Hypertens 2011 September; 29 (9): 1820-8, see "CD▶CD25▶Foxp3▶regulatory T cells suppress cardiac fibrosis in the hypertensive heart".)

In order to confirm the influence of the regulatory T cells in Alzheimer's diseases, the regulatory T cell colonies of severe patients (Alzheimer Disease: AD) and mild patients were investigated. The result showed that the Treg expressing Program death receptor 1 was much expressed (see J Alzheimers Dis. 2010; 21(3):927-38, "PD1 negative and PD1 positive CD4+ T regulatory cells in mild cognitive impairment and Alzheimer's disease").

The regulatory T cells were activated using CD3 and then Parkinson's Disease (PD) was treated using the Adoptive transfer of the regulatory T cells (see J Leukoc Biol. 2007 November; 82 (5):1083-94. Epub 2007 Aug. 3. "Neuroprotective activities of CD4+ CD25+regulatory T cells in an animal model of Parkinson's disease").

For vaccination promotion, especially for the vaccine developed using part or all of a variety of pathogens, when the vaccination is made through a specific route of administration (particularly for mucosal vaccine), the vaccine effect hardly appears in many cases. In this case, it has been found that since there existed many regulatory T cells in the corresponding route of administration, the vaccine effect did not appear (see Journal of Immunology, 2007, 179, 5633-5638).

The compositions of the present invention may comprise, in addition to the active ingredient, pharmaceutically suitable and physiologically acceptable adjuvants. These adjuvants include excipients, disintegrating agents, sweetening agents, binding agents, coating agents, swelling agent, lubricants, glidants and solubilizing agents.

In addition, the compositions of the present invention may be preferably formulated and administered as a pharmaceutical composition comprising at least one pharmaceutically acceptable carrier in addition to the abovementioned active ingredient. For the composition formulated as a liquid solution, a pharmaceutically acceptable carrier is suitable for sterilization and living body, which can be used by mixing saline, sterile water, Ringer's solution, buffered saline, albumin injection solution, dextrose solution, maltodextrin solution, glycerol, ethanol and one or more ingredients thereof. Also, the other conventional additives such as antioxidants, buffers and bacteriostatic agents may be added as needed. Furthermore, the composition of the present invention may be formulated as injectable formulations, pills, capsules, granules or tablets such as aqueous solution, suspension or emulsion by further adding diluents, dispersants, surfactants, binders and lubricants. In addition, the present composition may be preferably formulated, according to each disease or ingredient, using the methods disclosed in Remington's Pharmaceutical Science, Mack Publishing Company, Easton PA as a suitable method in the art.

In the composition of the present invention, the pharmaceutical preparation form may be granules, powders, coated tablets, tablets, capsules, suppositories, syrups, juices, suspensions, emulsions, drops or injectable solutions and a sustained release preparation of the active compound.

The compositions of the present invention may be administered by a conventional method via intravenous, intraarterial, intraperitoneal, intramuscular, intraarterial, intraperitoneal, intrasternal, percutaneous, intranasal, inhalation, topical, rectal, oral, intraocular, or intracutaneous routes.

In the treatment method of the present invention, the term "effective amount" refers to the amount required to achieve the effect of suppressing the cancer. Thus, the "effective amount" of the active ingredient of the present invention may be adjusted depending on various factors, including the type of diseases, the severity of diseases, the type and content of the active ingredient and other components contained in the composition, the type of formulation, the age, body weight, general health condition, sex and diet of the patient, time of administration, route of administration and the secretion ratio of the composition, the period of treatment and the drug used simultaneously. For adults, the inhibitor of the gene or protein is preferably administered once to several times a day, at the following dosages: 0.01 ng/kg~10 mg/kg for siRNA, 0.01 ng/kg~10 mg/kg for shRNA, 0.01 ng/kg~10 mg/kg for antisense oligonucleotides to mRNA of the gene, 0.1 ng/kg~10 mg/kg for the compound, 0.1 ng/kg~10 mg/kg for the monoclonal antibody to the protein, 0.1 ng/kg~10 mg/kg for the small molecular compound, 0.1 ng/kg~10 mg/kg for the natural products, and 0.1 ng/kg~10 mg/kg for the bioavailability protein.

Advantageous Effects

Lrig1 according to the present invention is specifically expressed on Treg, thereby controlling the Treg. Therefore, the present Lrig1 can be used as a new target of immunosuppressive agents.

DESCRIPTION OF DRAWINGS

FIG. 1 shows a comparison of the expression levels of Lrig1 in non-contacted T cells, Th1, Th2, Th17, iTreg and nTreg through Micro array.

FIG. 2 shows the difference of the expression level of the regulatory T cell-specific Foxp3 gene as a positive control.

FIG. 3 shows a comparison of the expression level of Lrig1 in non-contacted T cells ($CD44^{low}$, $CD62L^{high}$) and memory T cells ($CD44^{high}$, $CD62L^{low}$) with the expression level of Foxp3+regulatory T cells through RT-PCRn (two times tests).

FIG. 4 shows a relative comparison of mRNA expression level of Lrig 1 in T cells.

FIG. 5(a) confirms the expression of Lrig 1 in $CD4^+$ $CD25^{high}$ cells, $CD4^+$ $CD25^{low}$ cells and $CD4^+Foxp3^+$ cells through Western blot, and (b) when $CD4^+CD25^{high}$ cells and $CD4^+$ $CD25^{low}$ cells were compartmented into only CD4 positive cells, compares these cells with the control antibody in each cell group, analyses the expression level of LRIG1 with FACS and shows the difference (%). It can be seen that the expression of Lrig1 is increased in the natural regulatory T cells (nTreg) (from 0% to 6.24%).

FIG. 6(a) confirms the expression reduction of LRIG1 by the reverse transcription polymerase chain reaction after delivering control siRNA and Lrig1-specific siRNA to proliferated $CD4^+Foxp3^+$, and (b) it can be seen that the regulatory T cells with reduced expression of LRIG1 does not greatly increase its number upon expansion. Here, the blue shows that expansion (proliferation) of Treg cells is not increased when Treg cells ($CD4^+CD25^{high}$) were treated with Lrig1-specific siRNA and that the non-treated Treg cells (red) were normally expanded. The blue is indicated as (siRNA+$CD4^+CD25^{high}$) and the red is indicated as ($CD4^+$ $CD25^{high}$).

FIG. 7 shows that, when naive T cells ($CD^+CD25^{low}$) stimulated with anti-CD3+anti-CD28mAb was cultured as in Treg cells ($CD4^+CD25^{high}$), the proliferation of activated T cells was effectively inhibited in Treg cells with high Lrig-1 expression in mixed lymphocyte reaction, but Treg cells with lowered Lrig-1 expression by treatment of Lrig 1—specific siRNA did not inhibit the expansion of cells. As such, this shows the relationship between the expression and immunosuppressive activity of LRIG1 in $CD4^+CD25^{high}$ cells (A). By re-confirming the study result of (A) using CFSE dilution reaction method, the expression LRIG1 in $CD4^+CD25^{high}$ cells is proven to be important in the immunosuppressive activity of Treg cells.

FIG. 8 shows RT-PCR test result using LRIG1-specific primer wherein B cells, CD8+T cells, naive CD4+T cells, effector CD4+T cells and Treg cells were isolated in mouse to isolate mRNA and then they are used as a template. It can be seen from the test result that LRIG1 is specifically much expressed in the regulatory T cells.

FIG. 9 shows RT-PCR test result using LRIG1-specific primer wherein naive CD4+T cells, effector CD4+T cells and Treg cells were isolated in mouse to isolate mRNA and then an activation signal is given to the cells by anti-CD3+ anti-CD28 mAb stimulation, mRNA is separated from each cell and they are used as a template. It can be seen from the test result that LRIG1 is specifically much expressed in the regulatory T cells and that the expression in the activated regulatory T cells is highly induced.

FIG. 10 and FIG. 11 are about the result wherein the proteins of several stimulated cells are subjected to Western blotting with mAb to LRIG1d, and the cell colonies through their FACS.

MODE FOR INVENTION

Advantages and features of the present invention and methods of accomplishing the same will be apparent with reference to the examples set forth in detail below. However, the present invention is not intended to be limited to the examples set forth herein, and it may be implemented in many different forms. These examples are only provided to complete the disclosure of the present invention and to sufficiently define the scope of the invention to a person with ordinary skill in the technical field to which the present invention pertains. The present invention will be only defined by the appended claims.

Example 1

Isolation and Culture of T Cells

C57BL6 ($H-2^b$) wild-type mice and Foxp3-GFP transgenic mice were used. All mice were bred in a clean condition (SPF) where the temperature and humidity were properly adjusted, and was used at the period of 8-12 week age in accordance with the animal experiment protocol approved by the Animal Experiment Commission of Yonsei University in Seoul.

The spleen cells of C57BL/6 rats were isolated to which the antibodies attached with anti-CD4-magnetic bead was added and passed through a magnetic activated cell analyzer (MACS) (MiltenyiBiotec), thus isolating CD4+cells (90-95%). Nest, in order to conduct MicroArray, the CD4+cells were stained with anti-CD4-antibody (Clone RM4-5, BD bioscience), anti-CD25− antibody (Clone 7D4, BD bioscience), anti-CD44− antibody (Clone IM7, BD bioscience) and anti-CD62L-antibody (Clone MEL-14, BD bioscience), and then non-contacted T cells (Naive T cells), $CD4^+$ $CD62L^+CD44^-CD25^-$, natural regulatory T cells (nTreg), $CD4^+CD25^{high}$ cells and $CD4^+CD25^{low}$ cells were isolated through the flow cytometry (FACS, BD FACSAria™ II).

The T cells were removed through non-contacted T cells, anti-Thy1.2 antibody and rabbit complement (Cedarlance Laboratories Limited) to which Antigen-Presenting Cells (APCs) isolated by radiation of 30 Gy (3000 rad) were added at a ratio of 1:5 and stimulated with anti-CD3 antibody 1 μg/mℓ (clone 145-2C11, BD bioscience) and anti-CD28 antibody 3 μg/mℓ (clone 37.51, BD bioscience). Next, the antibody differentiating into each group of the T cells was added with cytokines and the cells were cultured for 72 hours. IL-2 (100 U/mℓ) was added to the remaining cell group except for iTreg and further cultured for 4 days. The type and amount of antibodies for each group of cells were as follows:

Th1—anti-IL-4 (10 μg/Mℓ), IL-12 (10 ng/Mℓ), IL-2 (100 U/Mℓ)

Th2—anti-IFN-g (10 μg/Mℓ), anti-IL-12 (10 ng/Mℓ), IL-4 (5000 U/Mℓ) and IL-2 (100 U/Mℓ)

Th17—anti-IL-4 (10 μg/Mℓ), anti-IFN-λ(10 μg/Mℓ), anti-IL-12 (10 μg/Mℓ), TGF-β(5 ng/Mℓ), IL-6 (10 ng/Mℓ), IL-1β(10 ng/Mℓ)

iTreg—anti-IL-4 (10 μg/Mℓ), anti-IFN-λ(10 μg/Mℓ), anti-IL-12 (10 μg/Mℓ), TGF-β(5 ng/Mℓ), IL-2 (100 U/Mℓ)

In order to conduct a reverse transcription polymerase chain reaction (RT-PCR, Reverse transcription-PCR), the total RNA was extracted using kit (Allprep DNA/RNA Mini Kit™ Qiagen) in CD4$^+$CD25$^{low}$ cells and CD4$^+$CD25$^{hig}$ cells and then the complementary DNA (cDNAs) were synthesized using kit (Transcriptor High Fidelity cDNA Synthesis Kit™ Roche). The polymerase chain reaction was carried out using oligonucleotide primers and PCR composition (master mix, Qiagen) where the purified complementary DNBA was directly designed. The transcription factor foxp3 and gamma actin 1 (ACTG1) of the regulatory T cells (Treg) were used as a control group. Each primer sequence is as follows:

TABLE 1

Primers for protein amplification

| Protein | SEQ ID NO | Sequence | Direction |
|---|---|---|---|
| LRIG1 | 1 | ACCACCGTAGGCATCTTCAC | Forward |
|  | 2 | GAGCCACTGTGTGCTGTTGT | Reverse |
| FOXP3 | 3 | CCCTTGGCCCATCCCCAGGA | Forward |
|  | 4 | CCGAGCGTGGGAAGGTGCAG | Reverse |
| ACTG1 | 5 | GGCGTCATGGTGGGCATGGG | Forward |
|  | 6 | ATGGCGTGGGGAAGGGCGTA | Reverse |

Example 2

Identification of Lrig-1 surface protein specifically expressing to CD4$^+$CD25$^+$ nTreg Cells isolated from Example 1, i.e., CD4$^+$CD25$^{high}$ cells, CD4$^+$ CD25$^{low}$ cells and CD4$^+$Foxp3$^+$ cells were dissolved with RIPA cytolysis buffer (Sigma). The same amount of cell suspension was then subjected to electrophoresis through SDS PAGE gel and moved into the membrane. Western blot was conducted using anti-LRIG1-antibody (SantaCruz), anti-Foxp3-antibody (ebioscience), and anti-beta actin (Cell Signaling).

To the cells isolated with a flow cytometry through a surface protein staining, i.e., CD4$^+$CD25$^{high}$ cells and CD4$^+$ CD25$^{low}$ cells, anti-LRTG-antibody (R&D systems) and control antibody (Goat-IgG control, R&D systems) were added to compare the expression level of LRIG, reacted at a temperature of 4° C. for 30 minutes and then washed with FACS buffer (0.05% sodium azide, 0.5% BSA/PBS). The flow cytometric analysis was conducted with the flow cytometry (FACSCalibur, BD Bioscience).

Example 3

Identification of the Relationship Between Lrig-1 Expression in Treg and Treg Proliferation Mouse Lrig1-specific siRNAs (Thermo Fisher Scientific) was prepared into a liposome-siRNA complex (Lipofectamin 2000™ Invitrogen) and the amount of final siRNA was made as 5~50 pmol and then transfected in proliferated CD4$^+$Foxp3$^+$ T cells 1×10$^5$/2 mℓ cell culture solution. After 24 hours, the reduction of expression was confirmed through the reverse transcription polymerase chain reaction. The Lrig1-specific siRNAs sequences used are as follows:

TABLE 2 siRNA for expression inhibition

| SEQ ID NO | Name | Sequence |
|---|---|---|
| 7 | SMARTpool siRNA J-046693-09 | CCGAACGGCCUGCGUAUAA |
| 8 | SMARTpool siRNA J-046693-10 | GGAGCCAGCUGAAGUCGUA |
| 9 | SMARTpool siRNA J-046693-11 | GGUCUGUAGUUGAGGACGA |
| 10 | SMARTpool siRNA J-046693-12 | CCUGGAAGGUGACGGAGAA |

Example 4

Identification of Relationship Between the Expression Reduction of Lrig-1 in Treg and the Suppressive Activity of Treg <Method for Suppressing a Mixed Lymphocyte Culture Reaction>

2.5×10$^5$ of C57BL/6 mouse-derived CD4$^+$CD25$^{low}$ T cells per each well were introduced in the 96-well plate immobilized with anti-CD3 antibody (clone 145-2C11) (5 μg/mℓ) to which anti-CD28 antibody (clone 37.51) (2.5 μg/mℓ) in an aqueous solution state was added and stimulated. The stepwise diluted nTreg and siRNA were added thereto. After one day, nTreg was added and subjected to mixed reaction in 5% CO$_2$ incubator at 37° C. for 72 hours. Before the final 6 hours, 1 μci of [$^3$H]-thymidine (185 GBq/mmol, Amersham Biosciences) per well was added. The cells were collected on filter paper using a cell harvester. The amount of [$^3$H]-thymidine incorporated within the cells was measured by TopCount NXT beta counter (PerkinElmer). Hence, it can be seen that the expression of LRIG1 in CD4$^+$CD25$^{high}$ cells is important in the immunosuppressive activity through the incorporation of [$^3$H]-thymidine after a mixed lymphocyte culture reaction (see FIG. 7(a)).

<CFSE Dilution Reaction (Carboxyfluorescein Succinimidylester)>

The CD4$^+$CD25$^{low}$ cells were pre-labeled with 1 μM CFSE (Sigma), and then 1×10$^6$ cells per well were introduced in 96-well plates immobilized with anti-CD3 antibody (clone 145-2C11) (5 μg/mℓ) and then stimulated in a CO$_2$ incubator at 37° C. for 48 or 96 hours. Also, anti-CD28-antibody (clone 37.51) (2.5 μg/mℓ) in an aqueous solution state was added and stimulated. The stepwise diluted nTreg and siRNA were added thereto. After one day, nTreg was added and subjected to mixed reaction in 5% CO$_2$ incubator at 37° C. for 72 hours. The anti-CD3 antibody (clone 4-5, BD bioscience) was added, reacted at a temperature of 4° C. for 30 minutes, washed with FACS buffer (0.05% sodium azide, 0.5% BSA/PBS). Before 10 minutes of the analysis, 7-AAD (ebioscience) was added, thus analyzing only the living cell. The CFSE dilution in CD4$^+$ cells was measured through FACSCalibur (BD Bioscience) to investigate the cell frequency and the proliferation times where the cell proliferation occurs. As a result, CD4$^+$CD25$^{low}$ cells stained with CFSE were subjected to mixed lymphocyte reaction. It can be seen that the expression of LRIG1 in CD4⁺CD25$^{high}$ cells is important in the immunosuppressive activity through the CFSE dilution degree (see FIG. 7(b)).

Example 5

Identification of Human Treg Cell-Specific Expression

Cells stimulated with anti-CD3+anti-CD28 mAb by isolation of human naive T cells, cells differentiated with iTreg by the treatment of anti-CD3+anti-CD28 mAb+TGFb+IL-2, cells treated with Rapamycin or Everolimus (inhibitors to inhibit proliferation of cells induced protein functions of mTOR and the derivatives thereof) known to induce the proliferation of Treg with the treatment of anti-CD3+anti-CD28 mAb+TGFb+IL-2, Jurkat human T cells, and naive human CD4+T cells were stimulated with anti-CD3+anti-CD28 mAb to isolate activated cells. The protein was prepared from each of these cells. Western blotting was conducted with mAb to LRIG1d. As a result, it can be seen that LRIG1d was specifically expressed only on iTreg and that the expression level is markedly increased in the activation and proliferation of Treg and proliferated iTreg. It has been shown that LRIG1 was greatly expressed even in the regulatory T cells of rats as well as in the regulatory T cells of human, particularly, the expression was increased in the activated or proliferated regulatory T cells (see FIG. 10 and FIG. 11).

The invention claimed is:

1. A method for screening an agent for Lrig (leucine-rich repeats and immunoglobulin-like domain) up-regulating activity comprising:
   (a) contacting the agent with a regulatory T cell expressing Lrig protein;
   (b) measuring an expression level of the Lrig expressed by the regulatory T cell; and
   (c) determining that the agent has Lrig up-regulating activity when the expression level of Lrig of the regulatory T cell is up-regulated.

2. The method of claim 1, wherein the Lrig protein is any one selected from the group consisting of Lrig1, Lrig2 or Lrig3.

3. The method of claim 1, wherein the Lrig protein is set forth in SEQ ID NO: 11.

4. The method of claim 1, wherein the expression level of Lrig by the regulatory T cell is determined by reverse transcription polymerase chain reaction (RT-PCR) or fluorescence-activated cell sorting (FACS).

5. The method of claim 1, wherein the agent for Lrig up-regulating activity is an immunosuppressive agent.

* * * * *